United States Patent [19]
Symchowicz et al.

[11] 3,944,675
[45] Mar. 16, 1976

[54] SUBSTITUTED ARYL AND ARALKYL AMIDES IN THE TREATMENT OF PARKINSONISM

[75] Inventors: Samson Symchowicz, Livingston, N.J.; Hans-Peter Faro, Grafing near Munich, Germany

[73] Assignee: Schering Corporation, Kenilworth, N.J.

[22] Filed: July 16, 1973

[21] Appl. No.: 379,524

Related U.S. Application Data

[63] Continuation of Ser. No. 341,624, March 15, 1973, which is a continuation of Ser. No. 198,974, Nov. 15, 1971, abandoned.

[52] U.S. Cl. ............... 424/324; 260/557 R; 260/404
[51] Int. Cl.² ........................................ A61K 31/165
[58] Field of Search ...... 424/324; 198/874; 260/557

[56] References Cited
UNITED STATES PATENTS 3,504,028  3/1970  Beregi et al. ........................ 260/557
3,689,504  9/1972  Horran ................................ 260/557

*Primary Examiner*—Stanley J. Friedman
*Attorney, Agent, or Firm*—Stephen B. Coan; Carver C. Joyner; Raymond A. McDonald

[57] ABSTRACT

Amides having aromatic substituents of the formula:

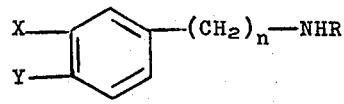

wherein R is an acyl radical derived from a carboxylic acid having from 3 to 20 carbon atoms, X and Y are members selected from the group consisting of hydrogen, fluoro, trifluoromethyl and hydroxy, and $n$ is an integer selected from the group consisting of 0, 1 and 2, exhibit an effect upon the central nervous system.

7 Claims, No Drawings

SUBSTITUTED ARYL AND ARALKYL AMIDES IN THE TREATMENT OF PARKINSONISM

This application is a continuation of our co-pending application Ser. No. 341,624, filed Mar. 15, 1973, which in turn is a continuation of application Ser. No. 198,974, filed Nov. 15, 1971 (now abandoned).

This invention relates to novel substituted aryl and aralkyl amides and to methods for their production. More particularly, the invention relates to amides derived from amines having aromatic substituents such as those derived from β-3,4-dihydroxy-phenethyl amine (dopamine). The invention also relates to methods for preparing and using such compounds.

The compounds of this invention are defined by the structural formula:

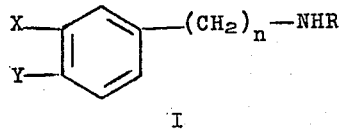

I wherein R is an acyl radical having from 3 to 20 carbon atoms; X and Y are members selected from the group consisting of hydrogen, fluoro, trifluoromethyl, and hydroxy; and $n$ is an integer selected from the group consisting of 0, 1 and 2.

The acyl radicals defined herein are derived from monobasic hydrocarbon carboxylic acids and may be straight chain, branched chain, cyclic and polycyclic carboxylic acids, also including bridged polycyclic carboxylic acids, i.e. those having at least three carbon atoms common to a pair of rings such as tricyclodecane (adamantane) carboxylic acid, bornane carboxylic acid, and the like. Also included are acyl radicals derived from such monobasic aromatic acids as benzoic and phenylacetic acids and the like.

The compounds of the instant invention (I) exhibit a substantial effect upon the central nervous system and are, particularly, valuable in alleviating the characteristic symptoms of parkinsonism. This degenerative disease of the nervous system is characterized by at least three classical abnormalities; rigidity, akinesia, and involuntary tremors.

BACKGROUND OF THE INVENTION

Recently, the known compound (−)-3-(3,4-dihydroxyphenyl)-L-alanine, (L-dopa) was found useful in the symptomatic treatment of parkinsonism. The use of L-dopa for such treatment was prompted by the finding that a relationship existed between the above-mentioned classical abnormalities and a biochemical deficiency of dopamine; it being known that certain enzymes were capable of converting L-dopa to dopamine. Thus, it was rationalized that the administration of L-dopa should increase the body's supply of dopamine and reduce the symptoms of Parkinsonism. The hypothesis was tested and proved valid. Since the observed therapeutic effect was believed to be due to the increased supply of dopamine, it was also reasoned that the administration of dopamine should also result in a reduction of the symptoms of Parkinsonism. Surprisingly, dopamine itself was found to be substantially ineffective in the treatment of such symptoms. Thus it is postulated that free dopamine is not transported across the blood-brain barrier and, therefore, does not give symptomatic relief. This being the case, it is surprising that certain amides of dopamine and of other substituted phenylamines exhibit such an effect.

PREPARATION OF THE PREFERRED EMBODIMENTS

The compounds of formula I wherein X and Y are other than hydroxy may be prepared by reacting the free amine or an acid addition salt thereof with the appropriate acylating agent, e.g. an acyl halide, preferably, in the presence of an acid acceptor to form the amide. The acid acceptors most frequently used in the art are tertiary amines, such as, pyridine, triethylamine, n-methyl piperidine and the like. Further, these tertiary amines may also be used as solvent for the reaction. In some instances, it may be convenient to use an excess of the amine being acylated as the acid acceptor. In those instances, the reaction may be effected in an inert organic solvent, such as an ether or an aromatic hydrocarbon e.g. diethyl ether, tetrahydrofuran, dioxane, benzene, toluene, xylene, or the like.

To illustrate the preparation of the compounds of formula I other than those wherein $R_2$ and $R_3$ are hydroxy, a phenyl amine or its mineral acid addition salt is dissolved or suspended with stirring in a suitable solvent, e.g. pyridine and an acyl halide or anhydride is carefully added dropwise or portionwise at about room temperature over about a 2 hour interval and the resulting suspension or solution is allowed to react for about 10 to 20 hours. The desired product is isolated by pouring the reaction mixture into an excess of a mixture of ice and a mineral acid with vigorous agitation whereupon the amide separates from the aqueous mixture, usually in the form of an oily mass, which may crystallize on continued agitation. However, it is usually preferable to extract the product with a water immiscible organic solvent followed by washing the extract with an aqueous solution of a weak base (e.g. sodium bicarbonate). The extract is then dried over a suitable drying agent (e.g. anhydrous sodium sulfate) and the solvent removed to yield the amide as an oily mass which may be crystallized from an appropriate solvent.

The foregoing reaction may be summarized by the following schematic representation:

SEQUENCE A

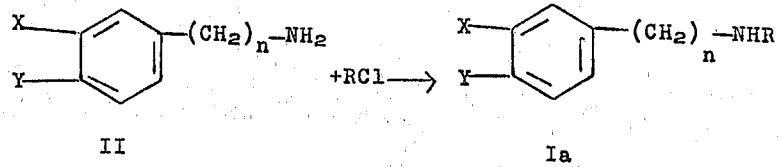

II          Ia wherein R and $n$ are as previously defined and X and Y are as previously defined excluding hydroxy.

The compounds of formula I wherein X and Y are hydroxy or either X or Y is hydroxy may be prepared from readily available compounds wherein the hydroxy function(s) or protected hydroxy function(s) are already extant. Exemplary of protected hydroxy functions are ethers, esters, or the like. For example, a dihydroxy aryl or aralkyl amine may be acylated to known procedures, such as the one described above, to form a diacyloxy aryl or aralkyl amide. The amide is then selectively hydrolyzed to yield the desired dihydroxy aryl or aralkyl amide. Selective hydrolyses are generally known in the art and are usually effected at ambient temperatures but may also be effected either at elevated temperatures for short time intervals or under refrigeration for extended periods of time. For example, the selective hydrolysis of such amides may be effected by subjecting an aqueous alcoholic solution of the compound to ammonium hydroxide at room temperature, preferably under an inert atmosphere, for from about 1 to about 8 hours preferably, about 5 hours and isolating the resulting dihydroxy amide.

The foregoing reactions may be summarized by the following schematic representation:

SEQUENCE B

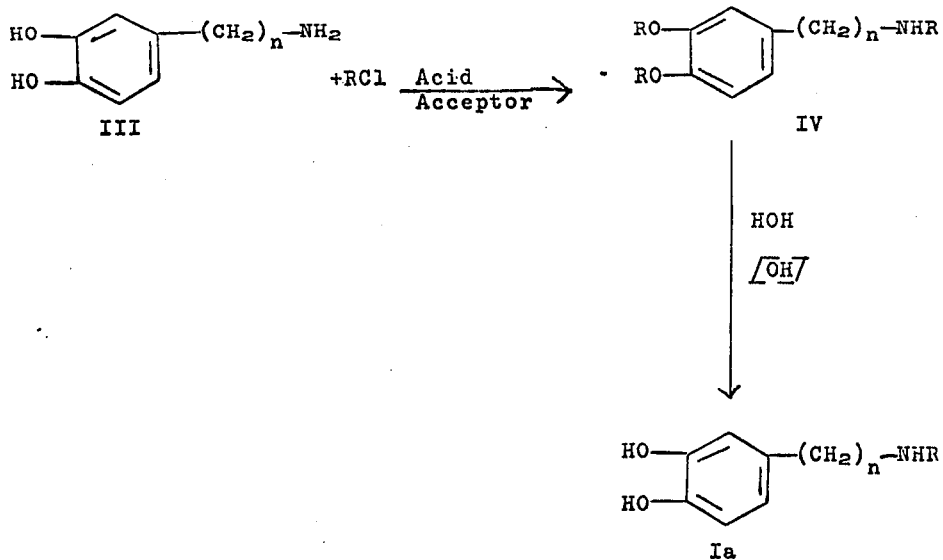

wherein R and $n$ are as previously defined.

Alternatively, the compounds of formula I wherein X and Y are hydroxy may be prepared from precursers having the hydroxy functions protected as ethers. Exemplary of such precursers are veratrylamine or homoveratrylamine (V) and piperonylamine, homopiperonylamine (VII) or the like. Such compounds are N-acylated by known methods and the free hydroxy function generated by treatment of the N-acyl compounds (VI) or (VIII) with known ether cleavage reagents, such as, boron tribromide, boron triiodide, lithium iodide, aluminum chloride or the like.

The foregoing reactions may be depicted by the following reaction sequences:

SEQUENCE C

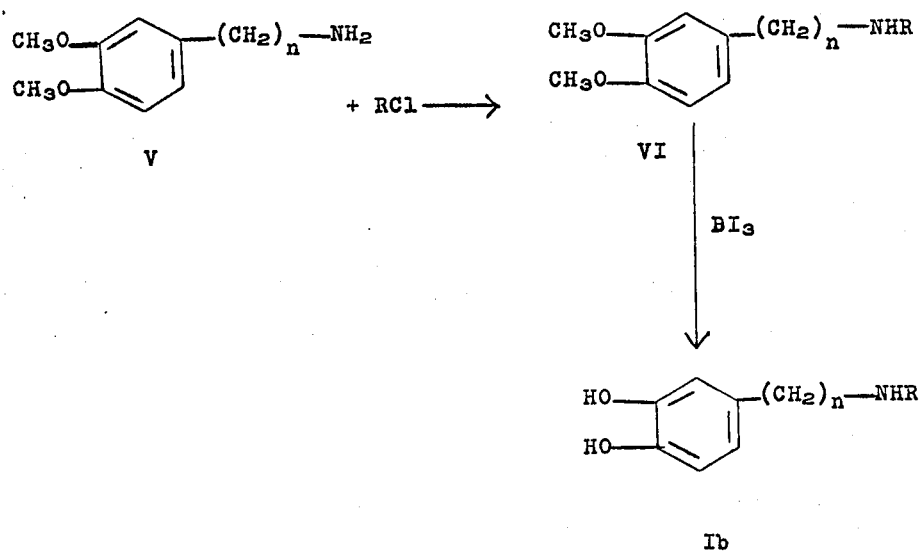

SEQUENCE D

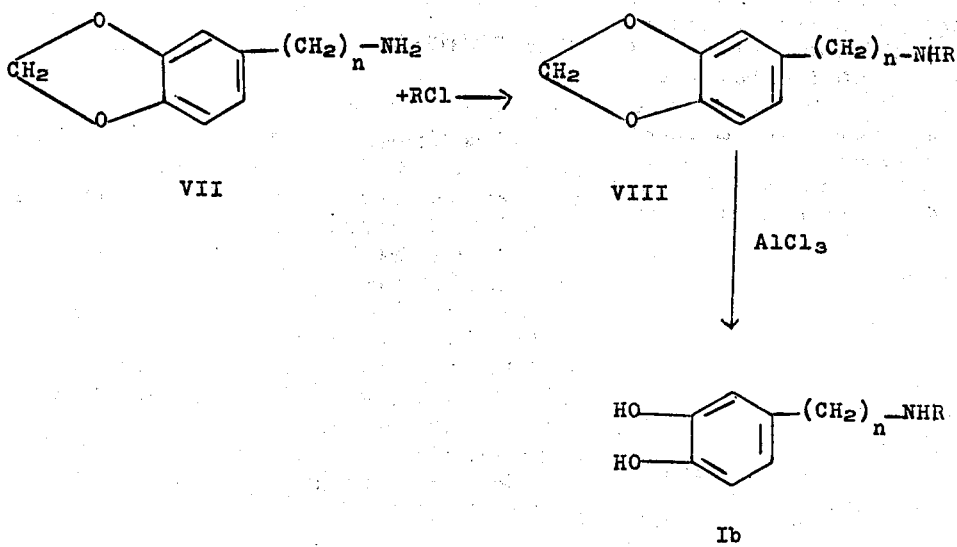

In each of reaction sequence C and reaction sequence D, R and n are as previously defined.

The compounds of formula I wherein X and Y are hydroxy may also be prepared from the corresponding dihydroxy amine by reacting the same with an acyl anhydride in an alcoholic solution. This method takes advantage of the favorable (more rapid) reaction rate of primary amines over those of the hydroxy groups. By the use of techniques generally known to the skilled art worker, the amide may be prepared in good yield and in a high state of purity.

The foregoing general procedures for preparing the compounds of formula I are specifically exemplified by the following examples.

EXAMPLE 1

N-[β-(3,4-Dihydroxyphenyl)-ethyl]-1-adamantanecarboxamide

Dissolve 15.0 g. of dopamine hydrochloride in 200 ml. of pyridine. With stirring, add 47.8 g. of 1-adamantane carboxylic acid chloride portionwise over a 2-hour period at room temperature. Stir at room temperature overnight. Add methanol (200 ml.), water (75 ml.) and concentrated ammonium hydroxide solution (50 ml.) to the reaction mixture and allow the clear solution to stand for 5 hours at room temperature. Pour the solution into 2 liters of 2N hydrochloric acid and ice with vigorous agitation. Extract the oily precipitate with ethyl acetate. Wash the extract with saturated aqueous sodium bicarbonate solution, dry over sodium sulfate and evaporate to a residue. Remove the last traces of ethyl acetate in vacuo and crystallize the product from acetone-ether to obtain the title product, m.p. 198°–200°C.

EXAMPLE 2

N-[[β-(3,4-Dihydroxyphenyl)-ethyl]-cyclopropanecarboxamide

Dissolve 15.0 g. of dopamine hydrochloride in 200 ml. of pyridine. Add with stirring 24.96 g. of cyclopropane-carboxylic acid chloride portionwise over a 2-hour period at room temperature. Stir at room temperature overnight. Add methanol (200 ml.), water (75 ml.) and concentrate ammonium hydroxide solution (50 ml.) to the reaction mixture and allow the clear solution to stand for 5 hours at room temperature. Pour the solution into 2 liters of of 2N hydrochloric acid and ice with vigorous agitation. Extract the oily precipitate with ethyl acetate. Wash the extract with saturated aqueous sodium bicarbonate solution, dry over sodium sulfate and evaporate to a residue. Dissolve the residue from ethyl acetate-ethyl ether and crystalline to obtain the title compound, m.p. 174.5°–176°C.

EXAMPLE 3

N-[β-(3,4-Dihydroxyphenyl)-ethyl]-n-decanoylamide

Dissolve 15.0 g. of dopamine hydrochloride in 200 ml. of pyridine. Add with stirring 46.1 g. of n-decanoyl chloride portionwise over a 2-hour period at room temperature. Stir at room temperature overnight. Add methanol (200 ml.), water (75 ml.) and concentrated ammonium hydroxide solution (50 ml.) to the reaction mixture and allow the clear solution to stand for 5 hours at room temperature. Pour the solution into 2 liters of 2N hydrochloric acid and ice with vigorous agitation. Extract the oily precipitate with ethyl acetate. Wash the extract with saturated aqueous sodium bicarbonate solution, dry over sodium sulfate and evaporate to a residue. Remove the last traces of ethyl acetate in vacuo and crystallize the product from an 8:2 ethyl ether:hexane mixture to obtain the title product, m.p. 71°–75°C.

EXAMPLE 4

N-[β-(3,4-Dihydroxyphenyl)-ethyl]-2,2-dimethylpropionamide

Dissolve 15.0 g. of dopamine hydrochloride in 200 ml. of pyridine. With stirring, add 28.8 g. of pivalyl chloride (α,α-dimethylpropionylchloride) portionwise over a 2-hour period at room temperature. Stir at room temperature overnight. Add methanol (200 ml.), water (75 ml.) and concentrated ammonium hydroxide solution (50 ml.) to the reaction mixture and allow the clear solution to stand for 5 hours at room temperature. Pour the solution into 2 liters of 2N-hydrochloric acid and ice with vigorous agitation. Extract the oily precipitate with ethyl acetate. Wash the extract with saturated aqueous sodium bicarbonate solution, dry over sodium sulfate and evaporate to a residue. Remove the last traces of ethyl acetate in vacuo and crystallize the product from a 9:1 toluene:ethanol mixture to obtain the title product m.p. 143.5°–146°C.

EXAMPLE 5

N-[β-(3,4-Dihydroxyphenyl)-ethyl]-2,2-dimethylpropionamide

A.

N-[β-(3,4-Dimethoxyphenyl)-ethyl]-2,2-dimethylpropionamide

Dissolve 1.3 g. of pivalyl chloride in 10 ml. of ethyl ether and add to a previously prepared solution of 1.0 g. of homoveratrylamine in a mixture of 20 ml. of ethyl ether and 5.0 ml. of triethylamine. Stir the mixture for 15 minutes, then add 20 ml. of water and 25 ml. of ethyl acetate. Separate the layers and extract the aqueous layer several times with ethyl acetate. Combine the organic phases and wash with 2N hydrochloric acid, saturated sodium bicarbonate solution, and water. Dry the organic layer over anhydrous sodium sulfate, filter and evaporate to a residue. Crystallize the residue from ether to obtain the product of this step, m.p. 78.0°–79.0°C. B. N-[β-(3,4-Dihydroxyphenyl)-ethyl]-2,2-dimethylpropionamide Dissolve 265 mg. of the product of step A in 15 ml. of methylene chloride and cool the solution to about −78°C. Add 335 mg. of boron triiodide and allow the reaction mixture to warm up to about 0°C with vigorous stirring. Stir the reaction mixture at about 0°C overnight, then add about 10 ml. saturated sodium bicarbonate solution. Acidify the mixture with 2N hydrochloric acid and extract with ethyl acetate. Decolorize the extract with aqueous sodium thiosulfate, then wash the extract successively with 2N-hydrochloric acid solution, saturated sodium bicarbonate solution, and water. Dry the extract over anhydrous sodium sulfate and evaporate to a residue. Crystallize the residue from a toluene-ethanol mixture to obtain the title product, m.p. 143°–146°C.

EXAMPLE 6

N-[β-(3,4-Dihydroxyphenyl)-ethyl]-cyclohexanecarboxamide

A.

N-[β-(3,4-Dimethoxyphenyl)-ethyl]-cyclohexanecarboxamide

Dissolve 2.0 g. of cyclohexane carboxylic acid chloride in 10 ml. of ethyl ether and add to a previously prepared solution of 2.0 g. of homoveratrylamine in a mixture of 20 ml. of ethyl ether and 5.0 ml. of triethylamine. Stir the mixture for 15 minutes, then add 20 ml. of water and 25 ml. of ethyl acetate. Separate the layers and extract the aqueous layers several times with ethyl acetate. Combine the organic phases and wash with 2N hydrochloric acid, saturated sodium bicarbonate solution and water. Dry the organic layer over anhydrous sodium sulfate, filter and evaporate to a residue. Crystallize the residue from ethyl acetate to obtain the product of this step, m.p. 110°–111°C.

B.

N-[β-(3,4-Dihydroxyphenyl)-ethyl]-cyclohexanecarboxamide

Dissolve 2.0 g. of the product of Step A carboxylate in 15 ml. of methylene chloride and cool the solution to about −78°C. Add 2.5 g. of boron triiodide and allow the reaction mixture to warm up to about 0°C with vigorous stirring. Stir the reaction mixture at about 0°C overnight, then add about 10 ml. saturated sodium bicarbonate solution. Acidify the mixture with 2N hydrochloric acid and extract with ethyl acetate. Decolorize the extract with aqueous sodium thiosulfate, then wash the extract successively with 2N hydrochloric acid solution, saturated sodium bicarbonate solution, and water. Dry the extract over anhydrous sodium sulfate and evaporate to a residue. Crystallize the residue from a toluene-ethanol mixture to obtain the title product 124°C – 126°C.

EXAMPLE 7

N-[β-(3,4-Dihydroxyphenyl)-ethyl]-1-adamantanecarboxamide

A.

N-[β-(3,4-Methylenedioxyphenyl)-ethyl]-1-adamantanecarboxamide

Dissolve 0.5 g. of homopiperonylamine in 5 ml. of ethyl ether and 2.5 ml. of triethylamine. The mixture is cooled in an ice-bath and a solution of 0.6 g. of 1-adamantane carboxylic acid chloride in 10 ml. of ethyl ether added dropwise. Stir the mixture for an additional 3 hours. Add water and extract the mixture with ethyl acetate. Wash the ethyl acetate extract with 2N hydrochloric acid, saturated sodium bicarbonate solution, and water. Dry over anhydrous sodium sulfate, filter and evaporate the filtrate to a residue. Crystallize the residue from ethyl acetate to obtain the product of this step, m.p. 146°–148°C.

B.

N-[β-(3,4-Dihydroxyphenyl)-ethyl]-1-adamantanecarboxamide

Subject the product of step A to the process described in Example 6 Step B to obtain the title product.

EXAMPLE 8

N-[β-(3,4-Dihydroxyphenyl)-ethyl]-2,2-dimethylpropionamide

Mix 2.2 g. of lithium iodide trihydrate and 0.53 g. of N-[β-(3,4-dimethoxyphenyl)-ethyl]-2,2-dimethylpropionamide, as prepared in Example 5, step A, heat under nitrogen to 180° and hold for 6 hours. Allow the melt to cool to room temperature, then dissolve the solid mixture by shaking with an ethyl acetate-water mixture. Separate the layers and wash the ethyl acetate layer with 2N hydrochloric acid, water, saturated aqueous sodium thiosulfate, saturated sodium bicarbonate and water in the order set forth. Dry the ethyl acetate solution over anhydrous sodium sulfate, filter and evaporate to a residue. Crystallize the residue from a 9:1 mixture of toluene:ethanol to obtain the title product.

EXAMPLE 9

N-[β-(3,4-Dihydroxyphenyl)-ethyl]-2,2-dimethylpropionamide

Suspend 0.86 g. of lithium iodide in 10.0 ml. of S-collidine and add 0.53 g. of N-[β-(3,4-dimethoxyphenyl)-ethyl] 2,2-dimethylpropionamide (see Example 5, step A). Reflux the mixture for 3 hours with vigorous stirring, then cool to room temperature. Extract the two liquid phases with ethyl acetate and water and proceed as described in Example 8 to obtain the product of this example.

EXAMPLE 10

N-[β-(3,4-Dihydroxyphenyl)-ethyl]-2,2-dimethylpropionamide

Dissolve 0.53 g. of N-[β-(3,4-dimethoxyphenyl)-ethyl]-2,2-dimethylpropionamide in 10 ml. of benzene and 15 g. of aluminum chloride. Reflux the mixture overnight (17 hours) with vigorous stirring. Cool the mixture to room temperature and, cautiously, pour the reaction mixture into dilute hydrochloric acid and ice with vigorous stirring. Separate the liquid phases and discard the benzene layer. Extract the aqueous layer with ethyl-acetate, then wash the extract with saturated sodium bicarbonate and water. Dry the extract over anhydrous sodium sulfate, filter and vaporate to a residue. Crystallize the residue from a 9:1 mixture of toluene:ethanol to obtain the title product.

EXAMPLE 11

N-Phenyl-1-adamantanecarboxamide

Dissolve 2.0 g. (10 mmoles) of 1-adamantane carboxylic acid chloride in 20 ml. of ethyl ether and add to 3.0 ml. (32.9 mmoles) of aniline. Stir the mixture 15 minutes, then add 20 ml. of water and 25 ml. of ethyl acetate. Separate the layers and extract the aqueous layer several times with ethyl acetate. Combine the extracts and wash with 2N hydrochloric acid, saturated sodium bicarbonate solution, and water. Dry the extract over anhydrous sodium sulfate, filter and evaporate to a residue. Crystallize the residue from ethyl acetate to obtain the product of this example, m.p. 196°–199°C.

EXAMPLE 12

N-Benzyl-1-adamantanecarboxamide

Dissolve 2.0 g. of (10 mmoles) of 1-adamantane carboxylic acid chloride in 20 ml. of ethyl ether and add to 3.0 ml. (28.0 mmoles) of benzylamine and repeat the process of Example 11 to obtain the product of this example, m.p. 170°–172°C.

EXAMPLE 13

N-[β-(phenylethyl)]-1-adamantanecarboxamide

Subject 1.63 g. (8.2 mmoles) of 1-adamantane carboxylic acid chloride, 1.0 g. of phenylethylamine and 5.0 ml. of triethylamine to the process of Example 11 and obtain the title product, m.p. 131°–133°C.

EXAMPLE 14

N-(4-Methoxyphenyl)-1-adamantanecarboxamide

Subject 6.5 g. (33.0 mmoles) of 1-adamantane carboxylic acid chloride, 4.0 g. (33.0 mmoles) of p-anisidine and 10.0 ml. of triethylamine to the process of Example 11 and crystallize the residue obtained thereby from chloroform to yield the title product, m.p. 181°–184°C.

EXAMPLE 15

N-(3-Methoxyphenyl)-1-adamantanecarboxamide

Subject 6.5 g. of adamantane carboxylic acid chloride, 4.0 g. of m-anisidine and 10.0 of triethylamine to the process of Example 14 and obtain thereby the title product, m.p. 172°–174°C.

EXAMPLE 16

N-(3,4-Dimethoxyphenyl)-1-adamantanecarboxamide

Subject 1.35 g. (6.8 mmoles) of adamantane carboxylic acid chloride, 1.0 g. (6.5 mmoles) of 4-amino veratrole and 4.0 ml. of triethylamine to the process of Example 11 and obtain thereby the title product, m.p. 224°–226°C.

EXAMPLE 17

N-(3,4-Dimethoxybenzyl)-1-adamantanecarboxamide

Subject 4.0 g. (20 mmoles) of adamantane carboxylic acid chloride, 3.3 g. (20 mmoles) of veratrylamine and 10.0 ml. of triethylamine to the process of Example 11 and obtain thereby the title product, m.p. 120°–122°C.

EXAMPLE 18

N-(3,4-Dimethoxyphenylethyl)-1-adamantanecarboxamide

Subject 2.0 g. of adamantane carboxylic acid chloride 1.8 g. (10.0 mmoles) of homoveratrylamine and 5.0 ml. of triethylamine to the process of Example 11. Crystallize the residue obtained thereby from an ethyl acetate-ethyl ether mixture to obtain the title product, m.p. 132°–133°C.

EXAMPLE 19

N-(3-Fluorophenyl)-1-adamantanecarboxamide

Subject 3.6 g. (18 mmoles) of adamantane carboxylic acid chloride, 2.0 g. of m-fluoroaniline and 8.0 ml. of triethylamine to the process of Example 11. Crystallize the residue obtained thereby from a mixture of chloroform-hexane to obtain the title product, m.p. 174°–177°C.

EXAMPLE 20

N-(4-Fluorophenyl)-1-adamantanecarboxamide

Subject 2.29 g. of adamantane carboxylic acid chloride (11.5 mmoles) 1.11 g. (10 mmoles) of p-fluoroaniline and 4.0 ml. of triethylamine to the process of Example 11. Crystallize the residue obtained thereby from ethyl ether to yield the title product, m.p. 170°–171°C.

EXAMPLE 21

N-(3,4-Difluorophenyl)-1-adamantanecarboxamide

Subject 2.29 g. of adamantane carboxylic acid chloride (11.5 mmoles) 1.29 g. of (10 mmoles) 3,4-difluoro-aniline and 4.0 ml. of triethylamine to the process of Example 11. Crystallize the residue obtained thereby from ethyl ether to yield the title product, m.p. 168.5°–170°C.

EXAMPLE 22

N-(3-Trifluoromethylphenyl)-1-adamantanecarboxamide

Subject 2.0 g. of adamantane carboxylic acid chloride, 1.60 (10 mmoles) of m-trifluoromethylaniline and 5.0 ml. of triethylamine to the process of Example 11. Crystallize the residue obtained thereby from a methylene chloride-hexane mixture to obtain the title product, m.p. 171°–174°C.

EXAMPLE 23

N-(4-Trifluoromethylphenyl)-1-adamantanecarboxamide

Subject 2.0 g. of adamantane carboxylic acid chloride 1.6 g. (10 mmoles) of p-trifluoromethylaniline and 5.0 ml. of triethylamine to the process of Example 11. Crystallize the residue obtained thereby from a mixture of methylene chloride-hexane to obtain the product of this Example, m.p. 189°–193°C.

EXAMPLE 24

N-[β-(4-Hydroxyphenylethyl)]-1-adamantanecarboxamide

Dissolve 2.0 g. (14 mmoles) of β-(4-hydroxyphenyl) ethylamine (tyramine) in 25 ml. of pyridine and add portionwise over a 2 hour period 5.6 g. (28.0 mmole) of adamantane carboxylic acid chloride with stirring. Stir at room temperature overnight (about 17 hours). Pour the suspension into an excess of 2N hydrochloric acid and ice with stirring. Extract the product with ethyl acetate, wash the extract with saturated sodium bicarbonate followed by a water wash. Dry the extract over anhydrous sodium sulfate and evaporate to a residue. Crystallize the residue from a mixture of ethyl acetate-ethyl ether to obtain the title product, m.p. 195°–198°C.

EXAMPLE 25

N-(4-Methoxybenzyl)-1-adamantanecarboxamide

Subject 4.0 g. (29.0 mmoles) of p-methoxy-benzylamine, 5.7 g. (29.0 mmoles) of adamantane carboxylic acid chloride and 10 ml. of triethylamine to the process of Example 11. Crystallize the residue obtained thereby from chloroform to obtain the product of this Example, m.p. 91°–94°C.

EXAMPLE 26

N-(4-Hydroxybenzyl)-1-adamantanecarboxamide

Dissolve 3.0 g. of N-(4-methoxybenzyl)-1-adamantanecarboxamide in 25 ml. of methylene chloride and cool the solution to about −78°C. Add 2.6 g. of boron triiodide and allow the reaction mixture to warm up to about 0°C with vigorous stirring. Stir the reaction mixture at about 0°C overnight, then follow the procedure described in Example 6B and crystallize the residue obtained thereby from ethyl acetate to obtain the product of this Example, m.p. 196°–198°C.

EXAMPLE 27

N-(3,4-Dihydroxyphenyl)-1-adamantanecarboxamide

Subject 2.0 of N-(3,4-dimethoxyphenyl)-1-adamantanecarboxamide and 2.5 g. of boron triiodide to the procedure set forth in Example 6B. Chromatograph the residue obtained thereby on a column containing 35 g. of silica gel using as the eluent a methylene chloride:ethanol: conc. ammonia (90:10:4 v/v). Crystallize the product from chloroform to obtain the product of this Example, m.p. 196°–199°C.

EXAMPLE 28

N-(3,4-Dihydroxybenzyl)-1-adamantanecarboxamide

Subject 2.0 g. of N-(3,4-dimethoxybenzyl)-1-adamantanecarboxamide and 2.4 g. of boron triiodide to the procedure of Example 6B except both the aqueous layer and the ethyl acetate extract are evaporated to a residue. The residue from the aqueous layer is extracted with chloroform which is used to dissolve the ethyl acetate residue. Concentrate the chloroform solution to obtain the title product, m.p. 183°–184°C.

As is true for most classes of compounds suitable for any given purpose or purposes, certain of such compounds are found to be more desirable than others. In the instant invention, it is found that the preferred compounds are those compounds of formula I wherein the acyl radical (R) is a cyclic or a bridged polycyclic group and in those instances wherein there are two substituents on the phenyl ring, said substituents are identical. Further, the preferred compounds are also those wherein $n$ is either 0 or 2, i.e. wherein the nitrogen of the amide is either connected directly to the phenyl ring or is connected through an ethylene bridge. Particularly suitable compounds within the foregoing groups are:

N-[β-(3,4-dihydroxyphenyl)-ethyl]-1-adamantanecarboxamide,

N-phenyl-1-adamantanecarboxamide,

N-(3,4-difluorophenyl)-1-adamantanecarboxamide, and

N-[β-(3,4-dihydroxyphenyl)-ethyl]-cyclopropane carboxamide.

According to test results using rats having induced symptoms of Parkinsonism, the compounds of this invention, substantially reduced such symptoms when administered in the range of from about 1 to about 120 mg/kg of body weight per day. The compounds are preferably administered in the range of from about 12 to about 48 mg/kg/day in divided doses at intervals of about 4 hours. However, the dose to be administered is dependent upon the stage and severity of the symptoms and upon the animal species being treated.

The compounds of this invention may be administered by the oral route in the form of tablets, capsules, elixirs or the like. These dosage forms may include the usual pharmaceutical excipients such as starches, gums and alcohol bases. In addition, the compounds of this invention may be incorporated into a dosage unit together with such an analgesic to mitigate the pain incident to parkinsonism or similar disorders.

The compounds of this invention may also be administered by the injection of a parenteral solution or suspension containing the pharmaceutical excipients usually employed for such dosage forms.

The following are exemplary of the above-described dosage forms containing some of the excipients usually employed therewith.

| Capsule Formula | mg/Capsule |
|---|---|
| N-[β-(3,4-Dihydroxyphenyl)-ethyl]-1-adamantanecarboxamide | 200.00 |
| Lactose, U.S.P. | 139.00 |
| Sodium Lauryl Sulfate, U.S.P. | 10.00 |
| Corn Starch, Food Grade | 100.00 |
| Magnesium Stearate, U.S.P. | 1.00 |
| | 450.00 |

PROCEDURE

Blend and mill the N-[β-(3,4-dihydroxyphenyl)-ethyl]-1-adamantanecarboxamide, lactose, sodium lauryl sulfate and corn starch; add the magnesium stearate and mix. Fill the formulation into hard gelatin capsules.

| Tablet Formula | mg/Tablet |
|---|---|
| N-[β-(3,4-Dihydroxyphenyl)-ethyl]-2,2-dimethylpropionamide | 400.00 |
| Mannitol, U.S.P. | 172.00 |
| Pluronic F-68, Food Grade | 20.00 |
| Corn Starch, Food Grade | 80.00 |
| Polyvinylpyrrolidone | 25.00 |
| Magnesium Stearate, U.S.P. | 3.00 |
| | 700.00 |

PROCEDURE

Prepare a damp mass consisting of the active ingredient and all of the remaining components of the formulation except the magnesium stearate and the starch; dry the mass; reduce to granules; add the magnesium stearate and the starch; mix and compress into tablets.

| Aqueous Suspension | mg/ml |
|---|---|
| N-[β-(3,4-Dihydroxyphenyl)-ethyl]-1-adamantanecarboxamide | 1.0 |
| Methylcellulose | 5.0 |
| Polysorbate 80, U.S.P. | 5.0 |
| Benzyl Alcohol, NF | 9.0 |
| Sodium Chloride, U.S.P. | 9.0 |
| Water for Injection, U.S.P. q.s. | 1.0 ml. |

PROCEDURE

Under aseptic conditions, prepare a solution of all of the components of the formulation except the active ingredient. Add the active ingredient with agitation. When the active ingredient is thoroughly mixed with the remainder of the formulation, fill the mixture aseptically into sterile vials.

We claim:

1. A method of treating the symptoms of Parkinsonism which comprises administering to a mammal exhibiting such symptoms a therapeutically effective quantity of a compound of the formula:

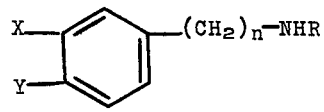

wherein R is an acyl radical derived from a hydrocarbon carboxylic acid having from 3 to 11 carbon atoms; X and Y are members selected from the group consisting of hydrogen, fluoro, trifluoromethyl and hydroxy; and $n$ is an integer selected from the group consisting of 0, 1 and 2.

2. A method of treating the symptoms of Parkinsonism which comprises administering to a mammal exhibiting such symptoms a therapeutically effective quantity of a compound of claim 1 of the formula:

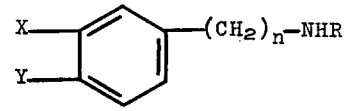

wherein R is an acyl radical derived from a hydrocarbon carboxylic acid having from 3 to 11 carbon atoms; X and Y are hydrogen; and $n$ is an integer selected from the group consisting of 0, 1 and 2.

3. A method of treating the symptoms of Parkinsonism which comprises administering to a mammal exhibiting such symptoms a therapeutically effective quantity of a compound of claim 1 of the formula:

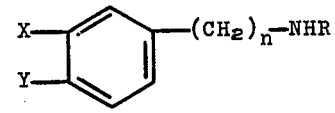

wherein R is an acyl radical derived from a hydrocarbon carboxylic acid having from 3 to 11 carbon atoms; X and Y are fluoro; and $n$ is an integer selected from the group consisting of 0, 1 and 2.

4. A method of treating the symptoms of Parkinsonism which comprises administering to a mammal exhibiting such symptoms a therapeutically effective quantity of a compound of claim 1 of the formula:

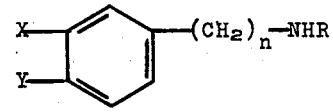

wherein R is an acyl radical derived from a hydrocarbon carboxylic acid having from 3 to 11 carbon atoms; X and Y are trifluoromethyl; and $n$ is an integer selected from the group consisting of 0, 1 and 2.

5. A method of treating the symptoms of Parkinsonism which comprises administering to a mammal exhibiting such symptoms a therapeutically effective quantity of a compound of claim 1 of the formula:

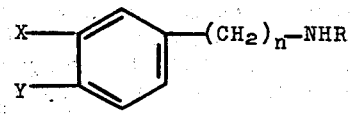

wherein R is an acyl radical derived from a hydrocarbon carboxylic acid having 3 to 11 carbon atoms; X and Y are hydroxy; and $n$ is an integer selected from the group consisting of 0, 1 and 2.

6. A method of treating the symptoms of Parkinsonism according to claim 5 which comprises administering to a mammal exhibiting such symptoms a therapeutically effective quantity of a compound of claim 10 wherein R is an acyl radical derived from a hydrocarbon carboxylic acid having 11 carbon atoms; X and Y are hydroxy; and $n$ is 2.

7. A method of treating the symptoms of Parkinsonism according to claim 6 which comprises administering to a mammal having such symptoms from about 1 to about 120 mg. of N-[β-(3,4-dihydroxyphenyl)ethyl]-1-adamantanecarboxamide per kg. of body weight per day.

* * * * *

UNITED STATES PATENT OFFICE
CERTIFICATE OF CORRECTION

Patent No. 3,944,675　　　　　　　　　Dated March 16, 1976

Inventor(s) Samson Symchowicz, et al.

It is certified that error appears in the above-identified patent and that said Letters Patent are hereby corrected as shown below:

Column 16, line 2 ---a compound of claim 10 wherein R--- should read ---a compound of claim 5 wherein R---

*Signed and Sealed this*

Twelfth *Day of* April 1977

[SEAL]

*Attest:*

RUTH C. MASON
*Attesting Officer*

C. MARSHALL DANN
*Commissioner of Patents and Trademarks*